(12) United States Patent
    Read

(10) Patent No.: US 9,459,038 B1
(45) Date of Patent: Oct. 4, 2016

(54) SYSTEM FOR DEFROST TERMINATION

(71) Applicant: Robert Michael Read, Vancouver, WA (US)

(72) Inventor: Robert Michael Read, Vancouver, WA (US)

(*) Notice: Subject to any disclaimer, the term of this patent is extended or adjusted under 35 U.S.C. 154(b) by 0 days.

(21) Appl. No.: 15/059,546

(22) Filed: Mar. 3, 2016

Related U.S. Application Data

(60) Provisional application No. 62/128,485, filed on Mar. 4, 2015.

(51) Int. Cl.
  *F25D 21/02* (2006.01)
  *F25B 47/02* (2006.01)
  *F25B 39/00* (2006.01)
  *F25D 21/00* (2006.01)
  *F25B 39/02* (2006.01)

(52) U.S. Cl.
  CPC .............. *F25D 21/02* (2013.01); *F25B 39/00* (2013.01); *F25B 47/02* (2013.01); *F25D 21/006* (2013.01); *F25B 39/02* (2013.01)

(58) Field of Classification Search
  CPC ...... F25D 21/02; F25D 21/006; F25B 47/02; F25B 39/00; F25B 39/02
  USPC .......................................... 62/151, 155, 272
  See application file for complete search history.

(56) References Cited

U.S. PATENT DOCUMENTS

| 4,045,971 | A | | 9/1977 | Brenner, Jr. | |
|---|---|---|---|---|---|
| 4,151,723 | A | * | 5/1979 | Gardner | F25B 5/02 62/155 |
| 4,232,528 | A | | 11/1980 | Behr | |
| 5,233,841 | A | * | 8/1993 | Jyrek | F25B 41/062 62/211 |
| 5,295,361 | A | * | 3/1994 | Novak | F25D 21/006 62/128 |
| 7,337,621 | B2 | | 3/2008 | Bagley et al. | |
| 2012/0023974 | A1 | * | 2/2012 | Park | F25D 21/006 62/80 |
| 2013/0031921 | A1 | * | 2/2013 | Hamada | F24F 13/222 62/155 |

* cited by examiner

*Primary Examiner* — Marc Norman
(74) *Attorney, Agent, or Firm* — Marger Johnson

(57) ABSTRACT

A system for controlling a defrost cycle of an evaporator having a sensor module and a control module. The sensor module includes a light source configured to emit light toward the evaporator when activated and to deactivate in response to a lockout signal. The sensor module also includes a light sensor configured to determine an amount of the emitted light reflected by the evaporator and to generate a detected light signal that corresponds to the amount of the emitted light reflected by the evaporator. The control module is configured to receive the detected light signal from the light sensor and to compare the detected light signal to a preset threshold. The control module is also configured to generate a termination signal when the detected light signal is less than the preset threshold and to generate the lockout signal when the detected light signal is greater than the preset threshold.

18 Claims, 7 Drawing Sheets

SYSTEM FOR DEFROST TERMINATION

CROSS-REFERENCES TO RELATED APPLICATIONS

This patent application claims the benefit of U.S. Provisional Application No. 62/128,485 filed on Mar. 4, 2015. That application is incorporated into this patent application by this reference.

FIELD OF THE INVENTION

This disclosure is directed to a system for defrost termination, and, more particularly, to a system for terminating a defrost mode of an evaporator for a refrigeration system.

BACKGROUND

Conventional refrigeration systems reduce the temperature of commercial and residential spaces, such as homes, offices, commercial freezers, and refrigerated delivery trucks. Such systems typically operate on the vapor-compression cycle and include four major components: a compressor, a condenser, an evaporator, and an expansion valve.

In conventional operation, refrigerant is compressed by the compressor and exits the compressor as a vapor at a temperature higher than the inlet temperature. The vapor is then condensed by the condenser, turning the vapor into a liquid. The expansion valve rapidly decreases the pressure of the liquid refrigerant, resulting in a mixture of liquid and vapor at a lower temperature and pressure. Next, the refrigerant passes through the evaporator. A fan typically blows relatively warm air, from the space being cooled or refrigerated, across the evaporator. As the warm air passes the evaporator, and more particularly, the fins or coils of the evaporator, the warm air vaporizes the refrigerant in the evaporator since heat from the air is transferred to the refrigerant in the evaporator. And the refrigeration cycle repeats. In this way, the temperature within the space to be cooled is reduced.

One drawback of such conventional systems is that frost tends to build up on the evaporator when moisture condenses out of the relatively warm air and freezes on the outside of the relatively cold evaporator. This happens mostly on the fins or coils of the evaporator. To reduce or eliminate such frost, conventional systems typically include a defrost operation mode, where the evaporator is heated so that its surface temperature is above the freezing point of water. In that way, frost on the evaporator is melted and the resulting water is either blown off by a fan or drips off of the evaporator, thus eliminating the frost and the condensed moisture.

Typically, conventional defrost modes are periodically initiated by a timer. In such systems, the defrost mode generally ends when the temperature of the evaporator increases to a certain level, such as a few degrees above the freezing point of water. The temperature of the evaporator may be read, for example, by a thermostat. Other conventional defrost systems use an infrared source to direct infrared radiation through the region where frost would accumulate on the evaporator. The radiation is received by an infrared detector on the opposite side of that region. In such systems, the infrared detector can determine if frost is present by detecting the presence or absence of infrared energy.

But there are shortcomings with the conventional systems. For example, since such systems initiate the defrost mode based on a timer, the systems might engage the defrost cycle even if no frost is present on the evaporator. This can lead to an unnecessary and inefficient use of electrical power. Also, infrared systems are typically expensive and require a large amount of labor to install and maintain because of their complexity.

Embodiments of the invention address these and other issues in the prior art.

SUMMARY OF THE DISCLOSURE

Embodiments of the disclosed subject matter provide mechanisms for terminating a defrost mode of a refrigeration system based on an absence of frost or ice on an evaporator rather than only on the temperature of the evaporator.

Accordingly, at least some embodiments of a system for controlling a defrost cycle of an evaporator may include a sensor module and a control module. The sensor module is configured to attach to the evaporator. The sensor module includes a light source configured to emit light toward the evaporator when activated and to deactivate in response to a lockout signal. The sensor module also includes a light sensor configured to determine an amount of the emitted light reflected by the evaporator and to generate a detected light signal that corresponds to the amount of the emitted light reflected by the evaporator. The control module is configured to receive the detected light signal from the light sensor and to compare the detected light signal to a preset threshold. The control module is also configured to generate a termination signal when the detected light signal is less than the preset threshold and to generate the lockout signal when the detected light signal is greater than the preset threshold.

In another aspect, at least some embodiments of a system for terminating a defrost cycle of an evaporator may include a sensor module, a control module, a set-point calibrator, and a defrost timer. The sensor module is configured to attach to the evaporator. The sensor module includes a light source configured to emit light toward the evaporator when activated and to deactivate in response to a lockout signal. The sensor module also includes a light sensor configured to determine an amount of the emitted light reflected by the evaporator and to generate a detected light signal corresponding to the amount of the emitted light reflected by the evaporator.

The control module includes a comparator circuit, a lockout circuit, and a termination relay. The comparator circuit is configured to compare the detected light signal to a preset threshold. The comparator circuit is also configured to generate a termination signal when the detected light signal is less than the preset threshold and to generate the lockout signal when the detected light signal is greater than the preset threshold. The lockout circuit is coupled to the comparator circuit and is configured to activate in response to the lockout signal to prevent the termination signal from reaching the termination solenoid of the defrost timer. The termination relay is coupled to the lockout circuit and is configured to relay the termination signal from the lockout circuit to the termination solenoid of the defrost timer.

The set-point calibrator is coupled to the control module and is configured to adjust and establish the preset threshold. The defrost timer is coupled to the control module. The defrost timer is configured to initiate a periodic defrost cycle of the evaporator and to provide electrical power to the control module only during the periodic defrost cycle. The defrost timer has a termination solenoid configured to terminate the defrost cycle in response to the termination signal.

In yet another aspect, at least some embodiments of a method of detecting frost in an evaporator may include activating a light source to emit light at the evaporator; determining, with a light sensor, an amount of the emitted light reflected by the evaporator; comparing, with a control module, a preset threshold to the amount of the emitted light reflected by the evaporator; generating a termination signal by the control module when the amount of the emitted light reflected by the evaporator coils is less than the preset threshold; generating a lockout signal by the control module when the detected light signal is greater than the preset threshold; and deactivating the light source in response to the lockout signal.

DETAILED DESCRIPTION

As described herein, embodiments of the invention are directed to a system for terminating defrost. In general, embodiments of the described system provide mechanisms for terminating a defrost mode of a refrigeration system based on an absence of frost or ice on an evaporator. In embodiments, the presence or absence of frost is determined by sensing visible light that is reflected from the evaporator. If frost is present, the amount of reflected visible light differs from the amount reflected when frost is absent.

Figure 1:
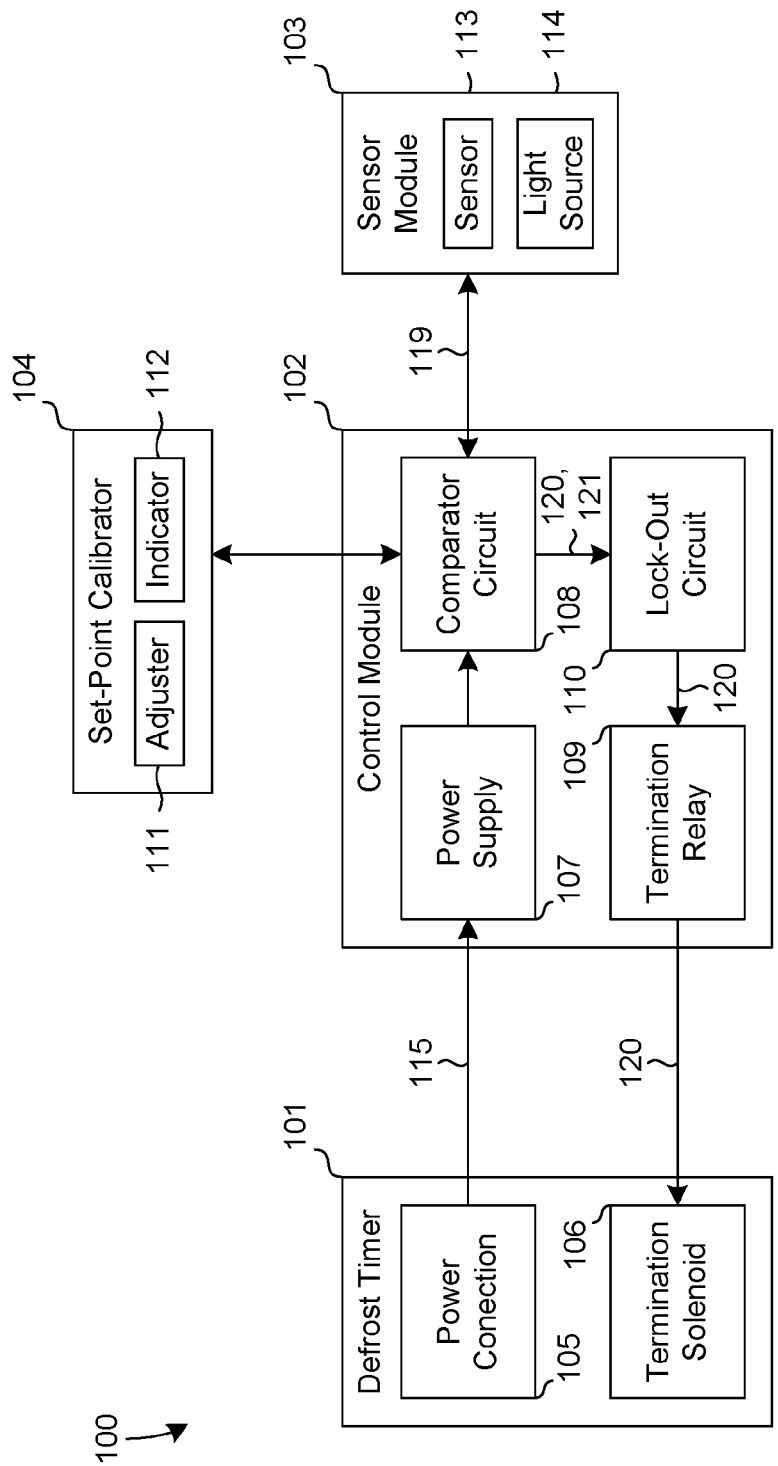
FIG. 1 is a functional block diagram of a system for defrost termination, according to embodiments of the invention.

FIG. 1 is a functional block diagram showing material portions of a system for defrost termination according to embodiments of the invention. As illustrated in FIG. 1, a system 100 for defrost termination may include a defrost timer 101, a control module 102, a sensor module 103, and a set-point calibrator 104. The defrost timer 101 may include a power connection 105 and a termination solenoid 106, and the control module 102 may include a power supply 107, a comparator circuit 108, a termination relay 109, and a lockout circuit 110. The set-point calibrator 104 may include an adjuster 111 and an indicator 112, while the sensor module 103 may include a sensor 113 and a light source 114.

The defrost timer 101 communicates with the control module 102, while the control module 102 communicates with the sensor module 103 and the set-point calibrator 104. The communication may be by way of one or more electronic couplings or connections.

The power connection 105 may be coupled to an outside power source, such as line, or mains, electric power. The power connection 105 provides electrical power 115 to the power supply 107. The power supply 107 may include an alternating current (AC) voltage to direct current (DC) voltage converter or rectifier. The sensor 113 may include, for example, a photocell, a photo resistor, or a light-variable resistor. The light source 114 may be any source of visible light that generates light that may be detected by the sensor 113. The visible light may be white light or another color. The visible light may be, for example, generated by an incandescent, fluorescent, or LED (light-emitting diode) source. For instance, the light source 114 may be an LED emitting white light at between 0.1 and 2 lumens, such as about 0.5 lumen.

In use, a user may preset a desired level, or a set-point, on the set-point calibrator 104, for example, by varying the adjuster 111, which may include an adjustable potentiometer. When the defrost timer 101 begins a defrost cycle or mode, the power connection 105 provides electrical power 115 to energize the control module 102, the sensor module 103, and the set-point calibrator 104.

Figure 2:
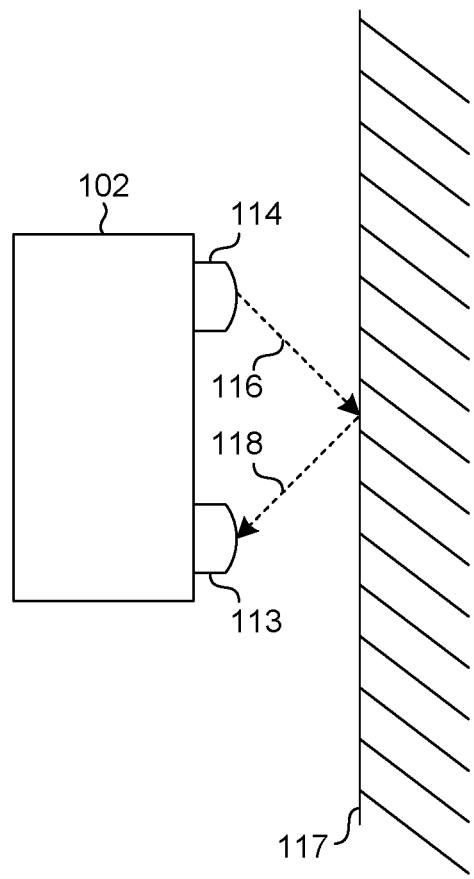
FIG. 2 is a diagrammatic, side view of an example sensor module, according to embodiments.
Figure 5:
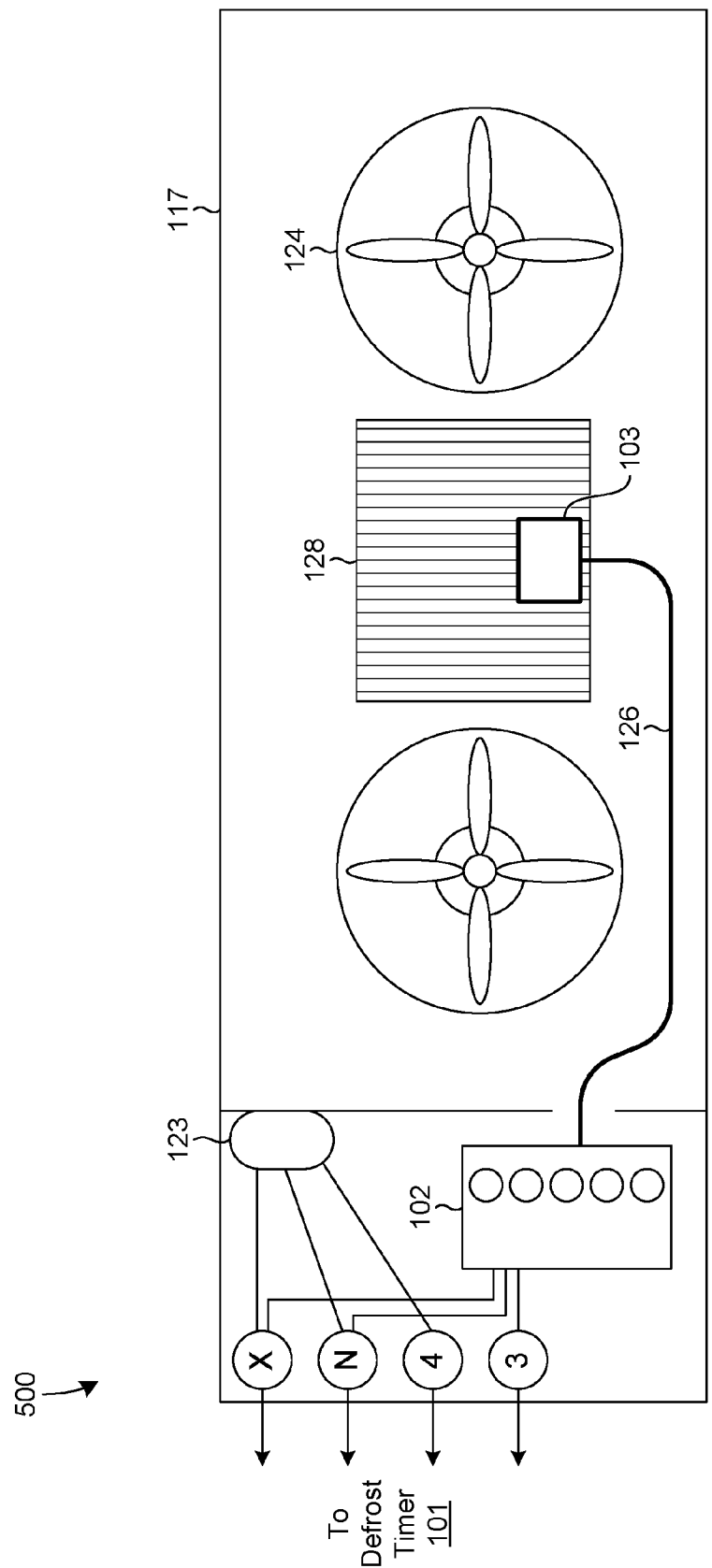
FIG. 5 is a diagrammatic front view of an example system for defrost termination installed on an evaporator assembly, according to embodiments.
Figure 6:
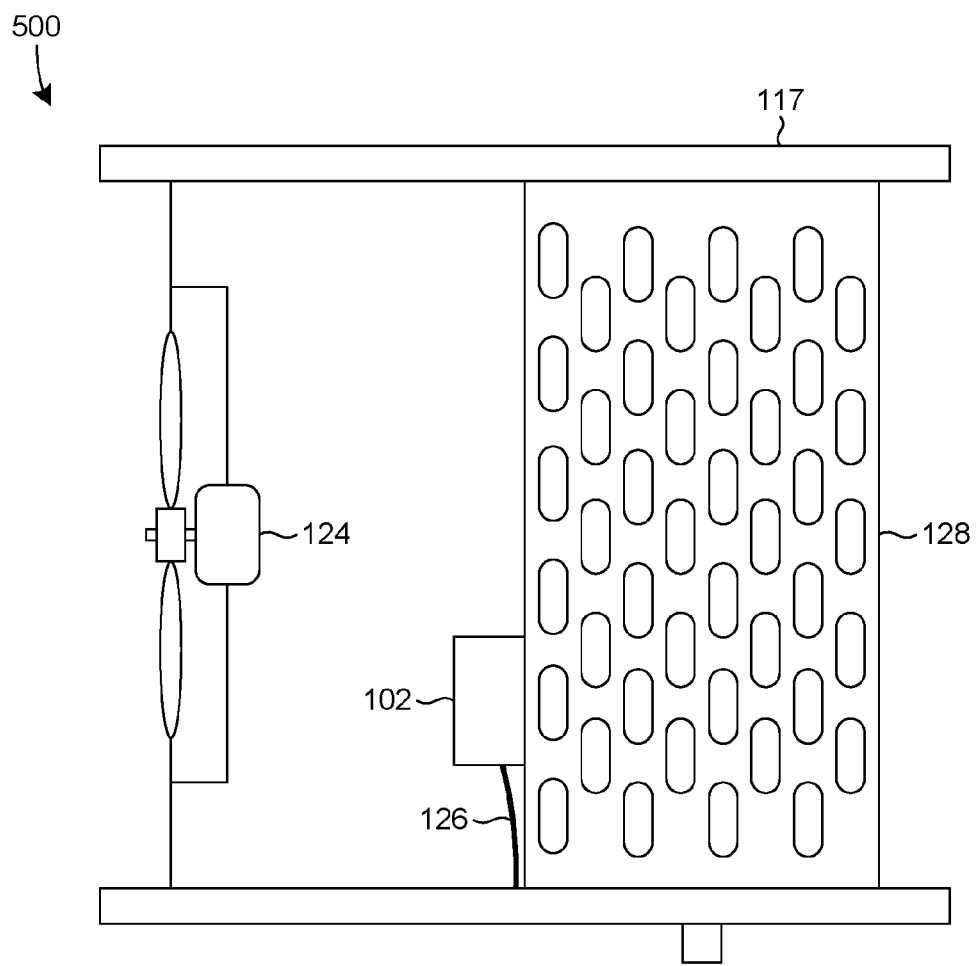
FIG. 6 is a side, diagrammatic view of the example system of FIG. 5.

With reference to FIGS. 1 and 2, when the control module 102 is activated, that is, when the power connection 105 energizes the control module 102, the light source 114 emits light 116 and illuminates at least a portion of an evaporator 117 of a refrigeration system, such as the evaporator 117 of FIGS. 5 and 6. The sensor 113 receives the reflected light 118 from the light source 114 that is reflected off of the evaporator.

Returning to FIG. 1, the sensor 113 generates a detected light signal 119, which corresponds to the amount of the emitted light 116 that is reflected by the evaporator. The comparator circuit 108 compares the detected light signal 119 to a threshold level that corresponds to the set-point preset by the user. If frost or ice is present on the evaporator, more light is reflected back to the sensor 113 than if frost or ice is not present. Thus, for example, the threshold level may be set to correspond to the detected light signal 119 at transition between the two states: with frost and without frost.

If the detected light signal 119 is below the threshold level for the set-point, the comparator activates the termination relay 109 in the control module 102. For example, the comparator 108 may generate a termination signal 120. The termination relay 109 then activates the termination solenoid 106. Thus, the defrost timer 101 exits the defrost mode and the power connection 105 stops energizing the control module 102. The control module 102 and the sensor module 103 then remain without power until the defrost timer 101 initiates the next defrost mode or cycle. In this way, the system 100 terminates the defrost cycle when the system 100 determines that no frost is present on the evaporator.

If the detected light signal 119 is above the threshold level for the set-point, the comparator circuit 108 locks out the termination relay 109 by activating the lockout circuit 110. For example, the comparator 108 may generate a lockout signal 121. This places the control module 102 in a sleep mode, and the light source 114 is turned off so that it no longer illuminates the evaporator. In this sleep mode, the defrost timer 101 may continue with the defrost cycle until the cycle terminates in a conventional manner. For example, a conventional termination thermostat may indicate that the evaporator has reached a temperature high enough to melt the frost on the evaporator and signal the termination solenoid 106 of the defrost timer 101 to terminate the cycle. As described above in the Background section, the termination thermostat is typically part of the evaporator in a conventional system that relies on the evaporator's temperature to end the defrost mode.

When the defrost timer 101 enters another periodic defrost cycle, the power connection 105 energizes the control module 102, and the described process repeats.

Figure 3:
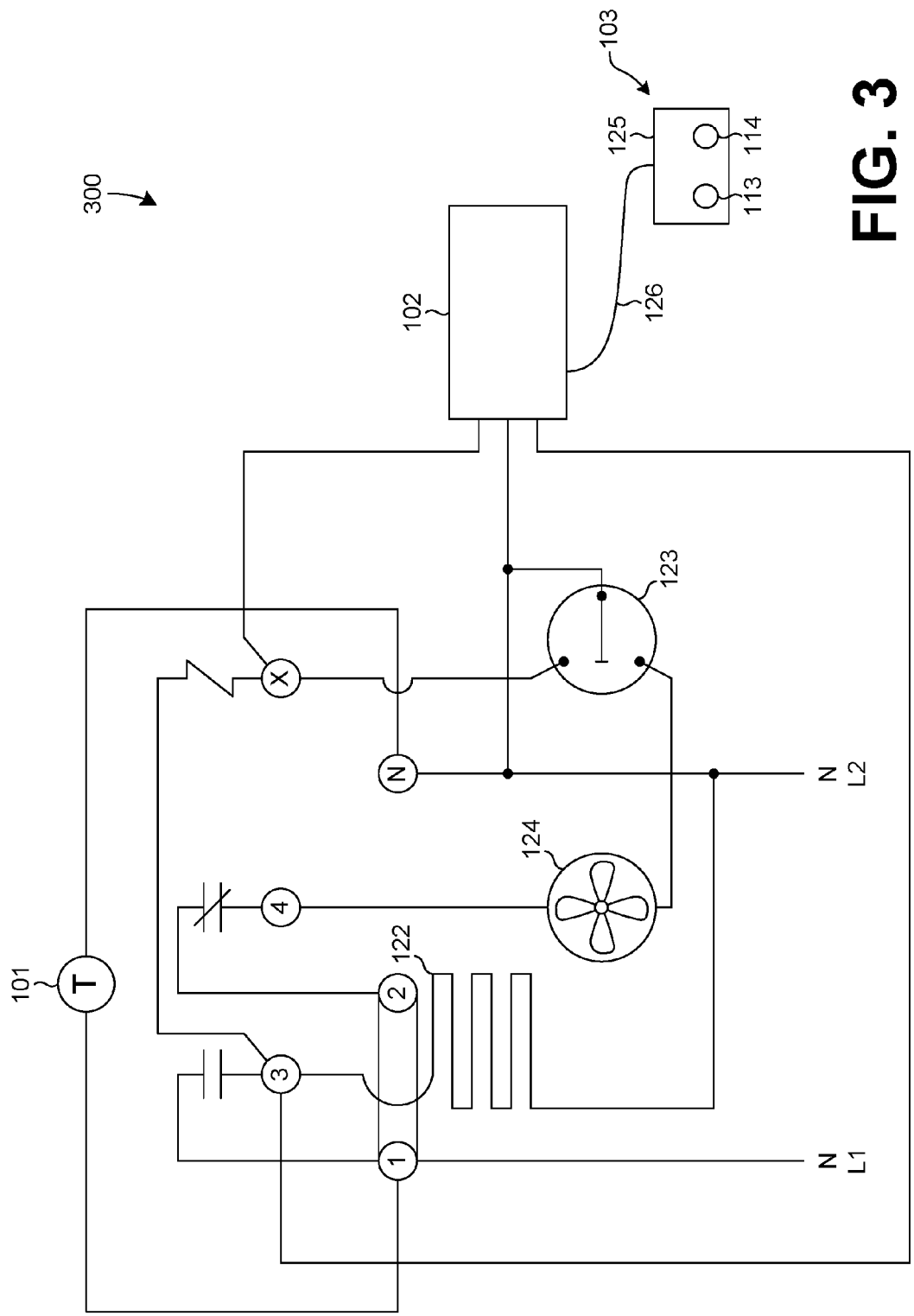
FIG. 3 is a partial schematic drawing of a system for defrost termination integrated with a conventional defrost heater system, according to embodiments.

The system for defrost termination may interact or be integrated with a conventional defrost heater system. For example, FIG. 3 is a partial schematic drawing showing material portions of a system for defrost termination integrated with a conventional defrost heater system, according to embodiments of the invention. As illustrated in FIG. 3, a system 300 for defrost termination may include a defrost timer 101, a control module 102, a sensor module 103, a sensor 113, and a light source 114. The comparator circuit 108, the termination relay 109, and the lockout circuit 110 may be within the control module 102 as illustrated in FIG. 3. These features are generally as described above for FIG. 1.

Also illustrated in FIG. 3 are a defrost heater 122, a defrost termination and fan delay switch 123, and an evaporator fan 124. Those components, along with the defrost timer 101, are typically already included in a conventional evaporator.

The sensor module may include one or more clips or hangers to mount or attach the sensor module to an evaporator, such as the evaporator 117 shown in FIGS. 5 and 6. The clips, for example, may be one or more alligator clips connected to the sensor module. The hanger may be, for example, one or more hooks configured to suspend the sensor module from a portion of the evaporator. The sensor module 103 may be connected to the control module 102 with a connecting cable 126.

Figure 4A:
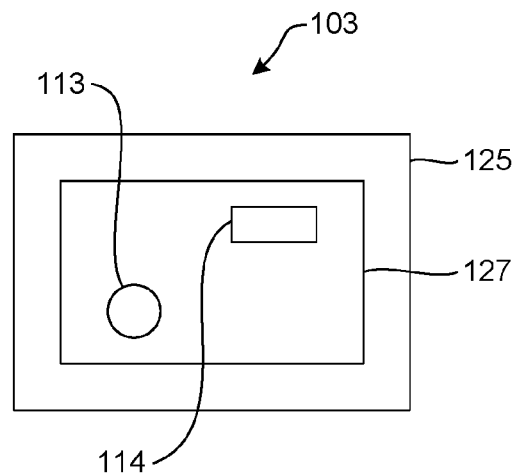
FIG. 4A is a diagrammatic, front view of an example sensor module, according to embodiments.
Figure 4B:
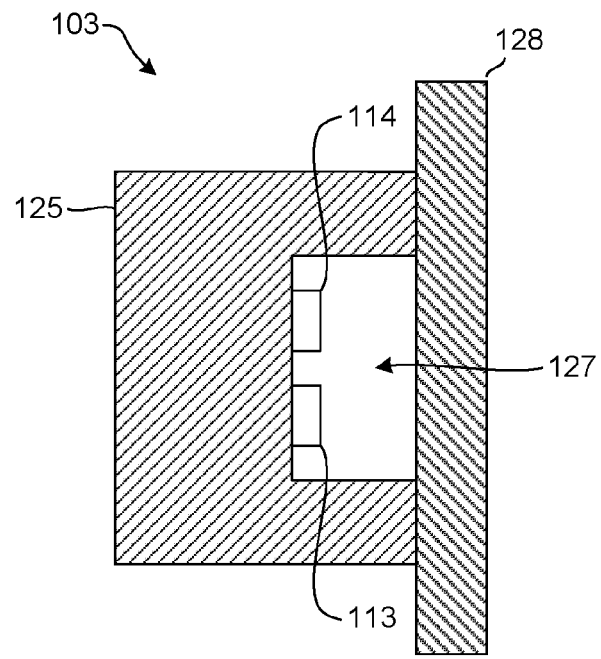
FIG. 4B is a diagrammatic, side, sectional view of the sensor module of FIG. 4A shown in relation to an evaporator coil.

Preferably, the sensor module 103 is configured to shield the sensor 113 from ambient light that might interfere with the desired operation of the sensor 113. As used here, ambient light is light other than the emitted light of the light source 114. Thus, for example, the sensor module 103 may partially enclose or encapsulate the sensor 113 in a housing 125 having an opening 127 for the sensor 113 to receive light from outside of the housing 125. An example of this is shown in FIGS. 4A and 4B. The opening 127 of the housing 125, containing the sensor 113, may be placed against the coils 128 of the evaporator 117. Preferably, the opening 127 of the housing 125 is immediately adjacent the evaporator coils 128. As an example, the opening 127 of the housing 125 may be no farther than about 1/32 of an inch (about 0.8 mm) from the evaporator coils 128. The light source 114 may also be enclosed or encapsulated with the sensor 113.

Returning to the example illustrated in FIG. 3, when the defrost timer 101 activates a defrost cycle, such as discussed above, contact points N and 3 of the defrost timer 101 provide power to the sensor module 103. The defrost timer 101 preferably operates on any voltage from about 100 VAC to about 240 VAC.

FIG. 5 is a front, diagrammatic view showing material portions of an example system 500 for defrost termination installed on an evaporator assembly, according to embodiments. FIG. 6 is a side, diagrammatic view of the system of FIG. 5. The illustrated evaporator assembly 117 includes evaporator fins and tubing 128, a fan and motor assembly 124, and a defrost-termination and fan-delay switch 123. The control module 102 may be mounted within the evaporator 117, or the control module 102 may be mounted at the defrost timer 101, which is typically remote from the evaporator 117. Other configurations are also possible. The sensor module 103 may be mounted on the fan side of the evaporator 117, such that the light source 114 faces the evaporator coils 128. The cable 126 connects the sensor module 103 to the control module 102. These features are generally as described above.

Thus, embodiments of the system for defrost termination may work with conventional defrost timers to improve the defrost process. For example, embodiments provide defrost capability with a more efficient use of electrical power since the defrost cycle can be terminated, if no frost is detected on the evaporator, before the temperature of the evaporator increases to the temperature set for the conventional thermostat. Also, embodiments of the system for defrost termination requires much less labor to install and maintain when compared to infrared systems, particularly since embodiments of the system for defrost termination may be mounted on just one side of the evaporator.

Accordingly, embodiments of the system for defrost termination interact, or are integrated, with a conventional defrost heater system for an evaporator 117 of a refrigeration system. When the conventional defrost timer 101 begins a defrost cycle, the control module 102 activates and the light source 114 illuminates at least a portion of the evaporator 117, such as the coils 128 of the evaporator. If frost or ice is present on the evaporator 117, more light is reflected back to the sensor 113, which is detected by the sensor module 103 and analyzed by the comparator circuit 108. The comparator circuit 108 then activates the lockout circuit 110, and the light source 114 turns off so that it no longer illuminates the evaporator 117. The defrost timer 101 then continues with the defrost cycle until a conventional termination thermostat terminates the defrost cycle. If frost or ice is not present on the evaporator 117, relatively less light is reflected back to the sensor 113. In such cases, the comparator 108 activates the termination relay in the control module 102, which in turn activates the termination solenoid 106 in the defrost timer 101. Accordingly, the defrost cycle ends, and the control module 102 is no longer energized.

Figure 7:
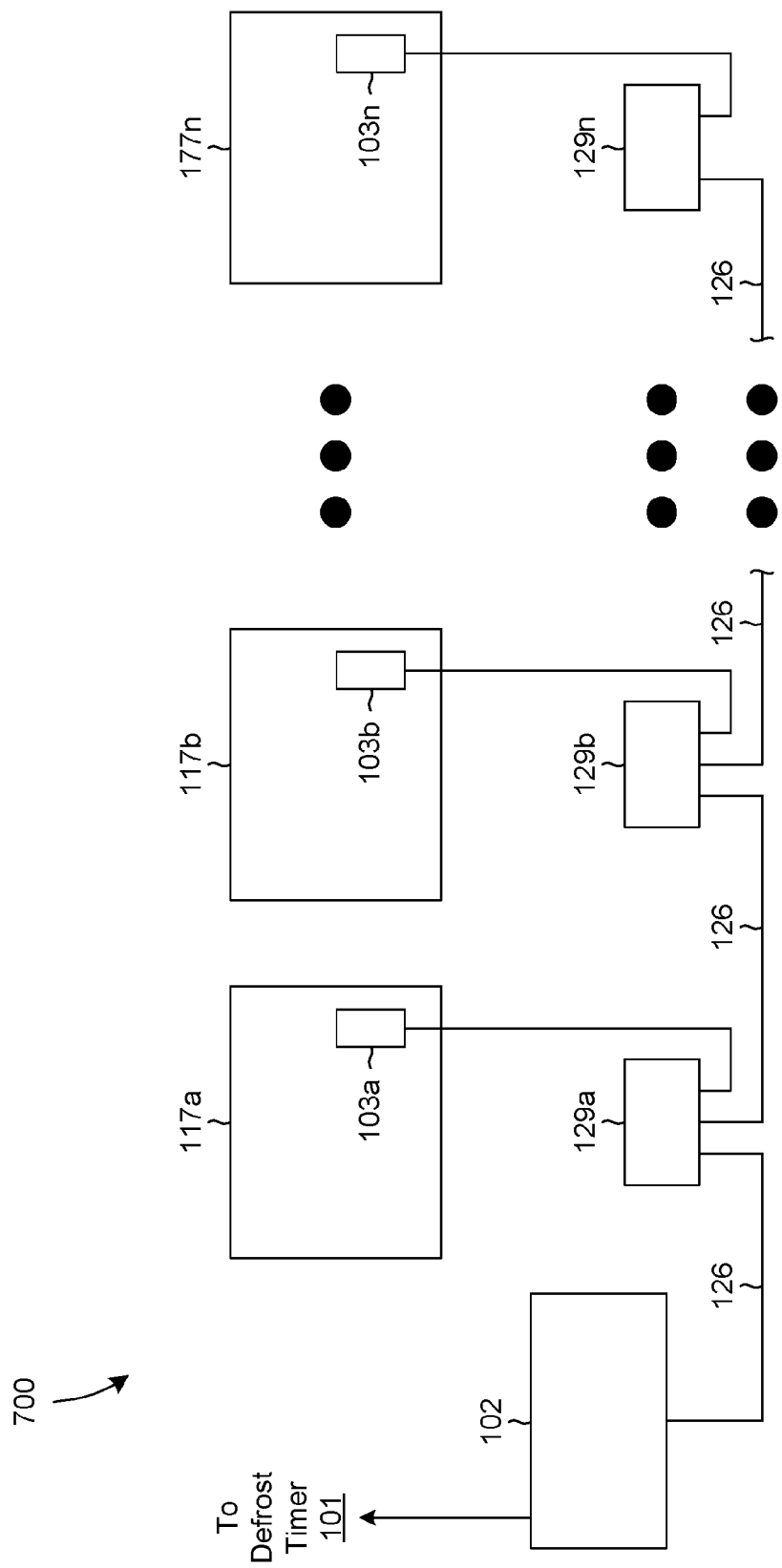
FIG. 7 is a diagrammatic view of an example system for defrost termination with multiple sensors, according to embodiments.

FIG. 7 is a diagrammatic view showing material portions of an example system for defrost termination with multiple sensors, according to embodiments of the invention. As illustrated in FIG. 7, a system 700 for defrost termination may include a control module 102 and a plurality of sensor modules 103a-103n that are remote from the control module 102. Each sensor module 103 in the plurality of sensor modules is attached to a different one of a plurality of evaporators 117a-117n. The control module 102 may be coupled to a defrost timer 101. Each sensor module 103 in the plurality of sensor modules is coupled to the control module 102, for example, by one or more connecting cables 126, and perhaps through a plurality of connectors 129a-129n. In this way, a single control module 102 may operate with a plurality of sensor modules 103 to terminate a defrost mode of each of the plurality of evaporators 117.

The previously described versions of the disclosed subject matter have many advantages that were either described or would be apparent to a person of ordinary skill. Even so, all of these advantages or features are not required in all versions of the disclosed apparatus, systems, or methods.

Additionally, this written description makes reference to particular features. It is to be understood that the disclosure in this specification includes all possible combinations of those particular features. For example, where a particular feature is disclosed in the context of a particular aspect or embodiment, that feature can also be used, to the extent possible, in the context of other aspects and embodiments.

Also, when reference is made in this application to a method having two or more defined steps or operations, the defined steps or operations can be carried out in any order or simultaneously, unless the context excludes those possibilities.

Furthermore, the term "comprises" and its grammatical equivalents are used in this application to mean that other components, features, steps, processes, operations, etc. are optionally present. For example, an article "comprising" or "which comprises" components A, B, and C can contain only components A, B, and C, or it can contain components A, B, and C along with one or more other components.

Although specific embodiments of the invention have been illustrated and described for purposes of illustration, it will be understood that various modifications may be made without departing from the spirit and scope of the invention. Accordingly, the invention should not be limited except as by the appended claims.

The invention claimed is:

1. A system for controlling a defrost cycle of an evaporator, the system comprising:
   a sensor module configured to attach to the evaporator, the sensor module including a light source configured to emit light toward the evaporator when activated and to deactivate in response to a lockout signal, and a light sensor configured to determine an amount of the emitted light reflected by the evaporator and to generate a detected light signal corresponding to the amount of the emitted light reflected by the evaporator;
   a control module configured to receive the detected light signal from the light sensor and to compare the detected light signal to a preset threshold, the control module also being configured to generate a termination signal when the detected light signal is less than the preset threshold, the control module further being configured to generate the lockout signal when the detected light signal is greater than the preset threshold; and
   a defrost timer coupled to the control module, in which the defrost timer is configured to initiate a periodic defrost cycle of the evaporator, in which the defrost timer is further configured to provide electrical power to the control module only during the periodic defrost cycle, the defrost timer having a termination solenoid configured to terminate a defrost cycle in response to the termination signal.

2. The system of claim 1, further comprising a set-point calibrator coupled to the control module, the set-point calibrator being configured to adjust and establish the preset threshold.

3. The system of claim 2, in which the set-point calibrator includes an adjustable potentiometer and an indicator light configured to illuminate when the preset threshold is established.

4. The system of claim 1, in which the control module further comprises:
   a comparator circuit configured to compare the detected light signal to the preset threshold;
   a lockout circuit coupled to the comparator circuit, the lockout circuit being configured to activate in response to the lockout signal to prevent the termination signal from reaching the termination solenoid of the defrost timer; and
   a termination relay coupled to the lockout circuit, the termination relay configured to relay the termination signal from the lockout circuit to the termination solenoid of the defrost timer.

5. The system of claim 1, in which the sensor module further includes a housing configured to shield ambient light from the light sensor, in which ambient light is light other than the emitted light of the light source.

6. The system of claim 1, in which the sensor module is a plurality of sensor modules remote from the control module, in which each sensor module in the plurality of sensor modules is coupled to the control module.

7. The system of claim 1, in which the sensor module is remote to the control module.

8. The system of claim 7, further comprising a cable connecting the sensor module to the control module.

9. A system for terminating a defrost cycle of an evaporator, the system comprising:
   a sensor module configured to attach to the evaporator, the sensor module including a light source configured to emit light toward the evaporator when activated and to deactivate in response to a lockout signal, and a light sensor configured to determine an amount of the emitted light reflected by the evaporator and to generate a detected light signal corresponding to the amount of the emitted light reflected by the evaporator;
   a control module including:
      a comparator circuit configured to compare the detected light signal to a preset threshold, the comparator circuit also being configured to generate a termination signal when the detected light signal is less than the preset threshold, the comparator circuit further being configured to generate the lockout signal when the detected light signal is greater than the preset threshold,
      a lockout circuit coupled to the comparator circuit, the lockout circuit being configured to activate in response to the lockout signal to prevent the termination signal from reaching the termination solenoid of the defrost timer, and
      a termination relay coupled to the lockout circuit, the termination relay configured to relay the termination signal from the lockout circuit to the termination solenoid of the defrost timer; and
   a set-point calibrator coupled to the control module, the set-point calibrator being configured to adjust and establish the preset threshold; and
   a defrost timer coupled to the control module, in which the defrost timer is configured to initiate a periodic defrost cycle of the evaporator and is further configured to provide electrical power to the control module only during the periodic defrost cycle, the defrost timer having a termination solenoid configured to terminate the defrost cycle in response to the termination signal.

10. The system of claim 9, in which the sensor module further includes a housing configured to shield ambient light from the light sensor, in which ambient light is light other than the emitted light of the light source.

11. The system of claim 10, in which the housing includes an opening and the light sensor is further configured to receive the emitted light reflected by the evaporator through the opening of the housing.

12. The system of claim 9, in which the sensor module is remote to the control module and the system further comprises a cable connecting the sensor module to the control module.

13. A method of detecting frost in an evaporator, the method comprising:
   initiating a periodic defrost cycle with a defrost timer coupled to a control module;

providing electrical power to the control module during the defrost cycle;

activating a light source to emit light at the evaporator;

determining, with a light sensor, an amount of the emitted light reflected by the evaporator;

comparing, with the control module, a preset threshold to the amount of the emitted light reflected by the evaporator;

generating a termination signal by the control module when the amount of the emitted light reflected by the evaporator coils is less than the preset threshold;

terminating the defrost cycle in response to the termination signal;

disconnecting the electrical power to the control module when terminating the defrost cycle;

generating a lockout signal by the control module when the detected light signal is greater than the preset threshold; and deactivating the light source in response to the lockout signal.

14. The method of claim 13, in which the light source and the light sensor are housed in a sensor module, the method further comprising attaching the sensor module to the evaporator and positioning the sensor module immediately adjacent to the evaporator.

15. The method of claim 13, in which the control module further comprises a set-point calibrator, the method further comprising establishing the preset threshold by adjusting the set-point calibrator.

16. The method of claim 15, further comprising activating a visual indicator when the preset threshold is established.

17. The method of claim 13, in which the evaporator is a plurality of evaporators, the method further comprising:

remotely coupling a plurality of light sources to the control module, in which activating a light source to emit light at the evaporator is activating a plurality of light sources, each light source emitting light at a different evaporator of the plurality of evaporators; and remotely coupling a plurality of light sensors to the control module, in which determining, with a light sensor, an amount of the emitted light reflected by the evaporator is determining, with a light sensor from the plurality of light sensors, an amount of the emitted light, from a corresponding light source of the plurality of light sources, reflected by the evaporator.

18. The method of claim 13, further comprising shielding the light sensor from ambient light, in which ambient light is light other than the light emitted by the light source.

* * * * *